United States Patent [19]

Kula et al.

[11] Patent Number: 4,590,161
[45] Date of Patent: May 20, 1986

[54] MICROBIOLOGICALLY PRODUCED L-PHENYLALANINE-DEHYDROGENASE, PROCESS FOR ITS RECOVERY AND USE

[75] Inventors: Maria-Regina Kula, Wolfenbüttel; Werner Hümmel, Brunswick; Horst Schütte, Salzgitter; Wolfgang Leuchtenberger, Bruchköbel, all of Fed. Rep. of Germany

[73] Assignees: Degussa Aktiengesellschaft, Frankfurt; Gesellschaft fur biotechnologisch Forschung, Stockheim, both of Fed. Rep. of Germany

[21] Appl. No.: 583,325

[22] Filed: Feb. 24, 1984

[30] Foreign Application Priority Data

Mar. 1, 1983 [DE] Fed. Rep. of Germany ....... 3307095

[51] Int. Cl.⁴ ...................... C12P 13/22; C12P 13/12; C12N 9/02; C12R 1/13

[52] U.S. Cl. .................... 435/108; 435/113; 435/189; 435/840

[58] Field of Search ................ 435/189, 190, 108, 113

[56] References Cited

U.S. PATENT DOCUMENTS 3,036,958 5/1962 Asai et al. ........................... 435/108
4,403,033 9/1983 Goto et al. ........................... 435/108

*Primary Examiner*—Lionel M. Shapiro
*Attorney, Agent, or Firm*—Cushman, Darby & Cushman

[57] ABSTRACT

The invention is directed to a microbiologically produced L-phenylalanine-dehydrogenase and a process for its recovery from Brevibacterium species DSM 2448. The new enzyme can be used for the enzymatic conversion of phenyl pyruvic acid, p-hydroxyphenyl pyruvic aid, indolyl pyruvic acid or 2-keto-4-(methylmercapto)-butyric acid into the corresponding L-α-aminocarboxylic acids.

19 Claims, 2 Drawing Figures

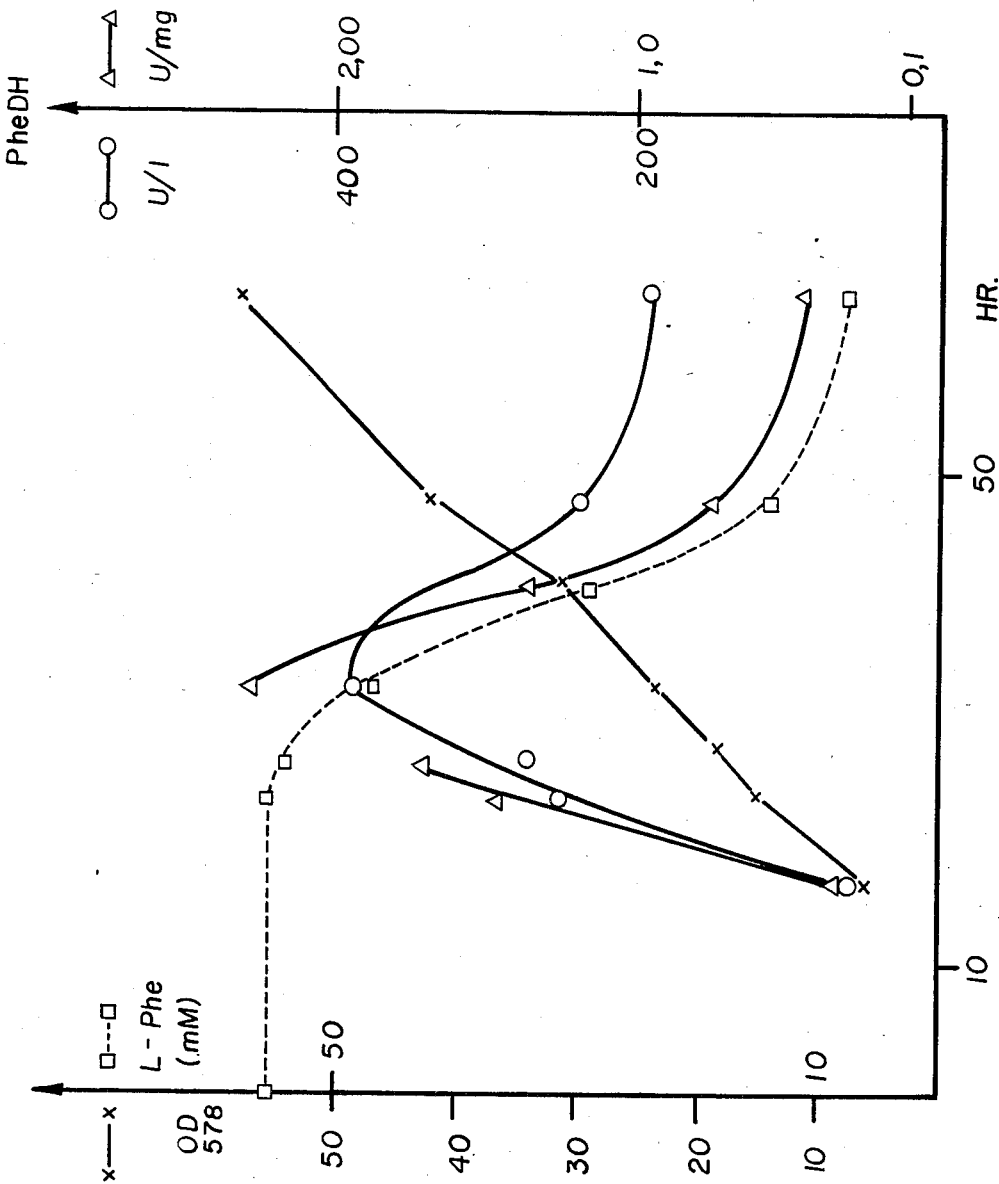

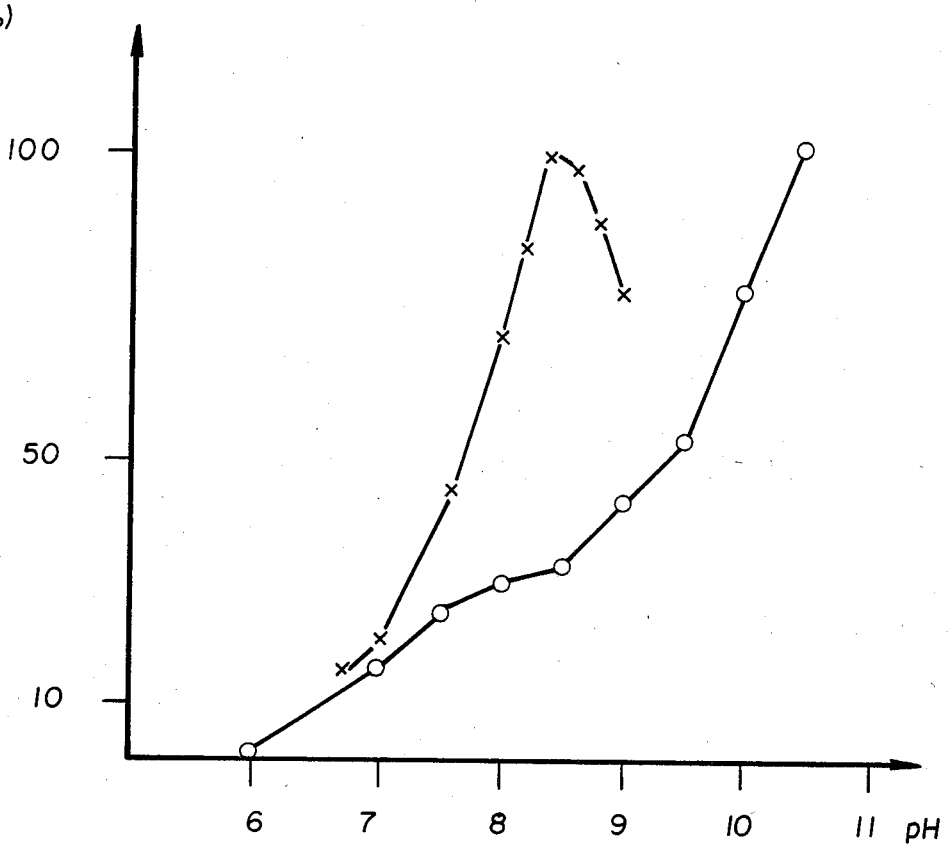

MICROBIOLOGICALLY PRODUCED L-PHENYLALANINE-DEHYDROGENASE, PROCESS FOR ITS RECOVERY AND USE

BACKGROUND OF THE INVENTION

The invention is directed to a previously non-described enzyme which catalyzes the following conversions

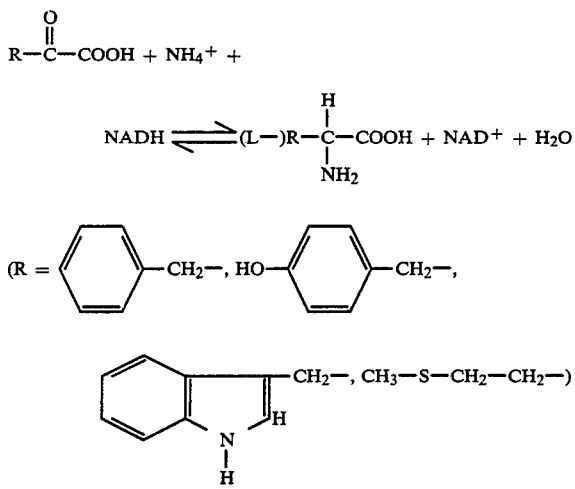

and to a process for recovery of the enzyme and to its use.

There are known enzymes by means of which L-glutamic acid and various other aliphatic L-α-aminocarboxylic acids, for example, L-alanine, L-valine, L-leucine, and L-isoleucine can be produced through reductive amination of the corresponding α-ketocarboxylic acids in the presence of ammonium ions and a coenzyme. While L-glutamic acid-dehydrogenase plays a central roll in the nitrogen metabolism and occurs ubiquitously, the reductive amination of other aliphatic α-ketocarboxylic acids is described above all, for enzymes from the bacillus genus. None of the previously known L-aminoacid-dehydrogenases, however, catalyze the conversion of aromatic or heteroaromatic α-ketocarboxylic acids into the corresponding L-aminocarboxylic aicds.

SUMMARY OF THE INVENTION

The L-phenylalanine-dehydrogenase of the invention is characterized by the following properties:

(a) it catalyzes the reductive amination of phenyl pyruvic acid to L-phenylalanine in the presence of ammonium ions and with NADH (nicotinamide-adenine-dinucleotide) as coenzyme, (b) it catalyzes the reductive amination of other α-ketocarboyxlic acids to the corresponding α-aminocarboxylic acids, especially of p-hydroxyphenyl pyruvic acid to L-tyrosine, of indolyl pyruvic acid to L-tryptophane and of 2-keto-4-(methylmercapto)-butyric acid to L-methionine, in the presence of ammonium ions and with NADH as coenzyme, (c) it catalyzes the oxidative desamination of L-phenylalanine, L-tyrosine, L-tryptophane and L-methionine with NAD+ as coenzyme, (d) it has an optimum pH region for the reductive amination of 8.5±1, and (e) it has an optimum pH region for the oxidative desamination of 10±1.

The L-phenylalanine-dehydrogenase of the invention can be obtained by means of a Brevibacterium strain which was deposited on Aug. 19, 1982 in the Deutschen Sammlung von Mikroorganisms (German Collection of Microorganisms) in Gottingen under the number 2448. The strain is characterized by the following morphological and biochemical properties.

Brevibacterium species DSM 2448 grows in short gram positive rods, which with increasing age transfer into cocci form. The cells are immobile and do not form spores. Growth is carried out strictly aerobically. No acid is formed from glucose. Catalase and nitrate reduction are positive, splitting of urea positive, gelatin, casein and starch breakdown negative, $H_2S$-formation negative, growth at 41° C. negative. There were detected as cell wall sugars arabinose, mannose, and galactose. The organism is strictly aerobic and thus differs from corynebacterium. The cell wall contains meso-diaminopimelic acid and thus differs from the genus Arthrobacter.

The spectrum of the cytochrome furthermore differentiates the organism from the genus Microbacterien. The newly discovered organism Brevibacterium species DSM 2448 at present cannot be assigned to any known type within the genus Brevibacterium. A series of strains of different types of Brevibacterium and different genuses, which in part are known as aminoacid producers were additionally grown under conditions under which Brevibacterium species DSM 2448 forms L-phenylalanine-dehydrogenase and tested for the ability to reductively aminate phenyl pyruvic acid in the presence of ammonium ions and NADH. In no case could the L-phenylalanine-dehydrogenase be detected.

To obtain the L-phenylalanine-dehydrogenase of the invention Brevibacterium species DSM 2448 is aerobically cultured in an aqueous nutrient medium which contains a source of carbon, nitrogen, thiamine, mineral salts, as well as an inductor, at a pH between 6.5 and 7.5 and a temperature between 25° and 32° C. The cell mass was separated off and the enzyme isolated from the cells. As inductors there can be employed for example, L-phenylalanine, D-phenylalanine, D,L-phenylalanine, D,L-phenylalanine ester, e.g. the methyl ester or L-histidine.

The L-phenylalanine-dehydrogenase of the invention can be obtained through a disintegration of the cells according to customary methods, e.g. ultrasonic treatment or wet grinding and separation of insoluble cell fragments in a soluble form. The enzyme activity is determined with a photometric test, by measuring the decrease of the adsorption of NADH at 340 nm. The test mixture contains 0.7M of ammonium chloride, adjusted with ammonia to pH 8.5, 0.20 mM of NADH, phenyl pyruvate and limiting amounts of enzyme. The enzyme activity is given in international units (U), whereby one unit signifies the decrease of 1μ mole NADH per minute. For the calculation there was employed a molar extinction coefficient of $6.22 \times 10^3$ at 340 nm. Even with the crude extract as catalyst there was detected per mole of NADH consumed 0.92 mole of L-phenylalanine formed under the test conditions on the aminoacid analyzer. That this was not due to a coupled reaction of a glutamate-dehydrogenase with subsequent transamination of phenyl pyruvate, was shown by the conversion in the membrane reactor where over 110 hours there could be detected a continuous formation of L-phenylalanine from phenyl pyruvate with regeneration of the molecular weight enlarged NADH with formate-dehydrogenase. The reaction rate of the catalyzed reaction is measured in relation of pH. The reductive amination is at a maximum at pH 8.5, the oxidative desamination increases until about pH 10.5. The highest reaction rate is found at a concentration of NADH of about 0.3 mmole/l. The reaction rate of the conversion increases with increasing ammonium ion concentration up to at least 0.5M ammonium ions. If the substrate concentration of the aromatic α-ketocarboxylic acids or of the aromatic L-aminocarboxylic acids is small compared to their $K_m$ value then the reaction rate depends linearly on the substrate concentration. This fact can be extended to a simple kinetic test for the determination of L-phenylalanine, L-tyrosine, L-tryptophane, phenyl pyruvic acid and hydroxyphenyl pyruvic acid. D-phenylalanine is not converted by the L-phenylalanine-dehydrogenase and on the other hand is an inhibitor of the oxidative desamination of L-phenylalanine. The L-phenylalanine produced in the enzyme membrane reactor through reductive amination of phenyl pyruvic acid was examined by polarimetry and treatment with D-AOD (D-aminoacidoxidase, Boehringer Mannheim) for optical purity. There could not be detected contamination by D-phenylalanine in the product using both methods. The product consisted of at least 99.99% of the L-enantiomer.

If Brevibacterium species DSM 2448 is grown on yeast extract, the crude extract catalyzes the conversion of a series of aromatic or heteroaromatic, as well as aliphatic, α-ketocarboxylic acids to the corresponding α-aminocarboxylic acids. This broad spectrum of convertible substrates permits the conjecture that under these growth conditions several enzyme activities are present in the crude extract.

Through fractional precipitation with ammonium sulfate and subsequent chromatography under salting out conditions with a decreasing ammonium sulfate gradient there results a 52 fold enrichment of the L-phenylalanine-dehydrogenase. A dehydrogenase is separated off by this chromatography which analogous to the L-leucine-dehydrogenase from Bacillus sphaericus catalyzes the conversion of the corresponding aliphatic α-ketocarboxylic acids to L-leucine, L-norleucine, L-valine, L-norvaline and L-isoleucine. The chromatographically purified L-phenylalanine-dehydrogenase furthermore catalyzes the reductive amination of the corresponding aromatic α-ketocarboxylic acids to L-phenylalanine, L-tyrosine and L-tryptophane, as well as 2-keto-4-(methylmercapto)-butyric acid to L-methionine. In further investigation it has been shown that the reductive amination of phenyl pyruvic acid, p-hydroxyphenyl pyruvic acid, indolyl pyruvic acid and 2-keto-4-methylmercapto)-butyric acid are catalyzed by the same enzyme protein. For this purpose on the one hand, there were experiments to induce various dehydrogenase activities by culturing in the presence of different α-aminocarboxylic acids. For this purpose Brevibacterium species DSM 2448 is grown in a medium containing 1% malt extract, 0.5% glucose, 2 μg thiamine/l, 0.2% $KH_2PO_4$ and different α-aminocarboxylic acids in a concentration of 1%. The pH of the medium was adjusted to 7.4. The cells were harvested after 24 hours growth at 30° C., broken up with ultrasonics and the reductive amination of 5 α-ketocarboxylic acids was tested in each extract by optical test. The formation of L-tryptophane from indolyl pyruvic acid was checked on the aminoacid analyzer because of the disturbance in the optical test with this substrate. The results are collected in Table 1:

TABLE 1

| Experiment Nr. | Inductor | $OD_{578}$ | Wet mass g/l | Protein mg/ml | α-Ketocarboxylic acid* 1 | 2 | 3 | Conversion U/ml 4 | 5 | 6 |
|---|---|---|---|---|---|---|---|---|---|---|
| 1 | L-Phe | 14,5 | 9,5 | 1,9 | 1,94 | 1,71 | 0,85 | 0,40 | 0 | 0 |
| 2 | D-Phe | 7,3 | 8,7 | 1,7 | 1,74 | 1,50 | 0,80 | 0,30 | 0 | 0 |
| 3 | D,L-Phe | 9,5 | 8,7 | 2,4 | 1,98 | 1,68 | 0,85 | 0,35 | 0 | 0 |
| 4 | L-His | 8,5 | 9,4 | 2,4 | 1,02 | 0,71 | 0,37 | 0,16 | 0 | 0 |
| 5 | L-Val | 18,1 | 23,3 | 3,3 | 0 | 0 | 0 | 0 | 0,15 | 1,28 |
| 6 | L-Norleu | 11,3 | 14,1 | 1,6 | 0 | 0 | 0 | 0 | 0,20 | 1,11 |
| 7 | L-Ile | 14,6 | 18,8 | 2,6 | 0 | 0 | 0 | 0 | 0,37 | 0,47 |
| 8 | L-Leu | 13,5 | 18,6 | 1,5 | 0 | 0 | 0 | 0 | 0,52 | 0,68 |
| 9 | L-Ala | 10,3 | 18,2 | 1,7 | 0 | 0 | 0 | 0 | 0 | 0 |
| 10 | L-Glu | 9,8 | 13,9 | 1,7 | 0 | 0 | 0 | 0 | 0 | 0 |
| 11 | $NH_4Cl$ | 12,1 | 11,2 | 1,1 | 0 | 0 | 0 | 0 | 0 | 0 |
| 12 | L-Phe—methyl-ester** | 18,0 | 10,0 | 1,7 | 1,51 | nb | nb | nb | nb | nb |

*α-Ketocarbonxylic acids employed for the reductive animation
1 Phenyl pyruvic acid
2 p-Hydroxyphenyl pyruvic acid
3 2-Keto-4-(methylmercapto)-butyric acid
4 Indolyl pyruvic acid
5 2-Keto-hexanoic acid
6 2-Keto-4-methylpentanoic acid
**Concentration in the medium only 0.5%
nb = not determined Table 1 shows that Brevibacterium species DSM 2448 produces two inducible L-aminoacid-dehydrogenases, one L-leucine-dehydrogenase and the other L-phenylalanine-dehydrogenase. The L-leucine-dehydrogenase converts from the tested α-ketocarboxylic acid, 2-ketohexanoic acid and 2-keto-4-methylpentanoic acid and is induced by L-norleucine, L-valine, L-isoleucine and L-leucine. The L-phenylalanine-dehydrogenase converts phenyl pyruvic acid, p-hydroxyphenyl pyruvic acid, indolyl pyruvic acid and 2-keto-4-(methylmercapto)-butyric acid and is induced by L-phenylalanine, D-phenylalanine, D,L-phenylalanine, L-histidine, and L-phenylalaninemethyl ester. These results are in accord with the experiment for the chromatographic separation of the two L-aminoacid-dehydrogenases.

Furthermore, there were experiments to atain a differential desactivation of the different dehydrogenase activities present in the crude extract by a heat denaturation at 52° C. Thereby it was shown that under these conditions the enzyme which catalyzed the reductive amination of 2-ketohexanoic acid and 2-keto-4-methylpentanoic acid having a uniform kinetic pattern is quickly desactivated. On the other hand, it showed that the enzyme catalyzing the reductive amination of phenyl pyruvic acid, p-hydroxyphenyl pyruvic acid, indolyl pyruvic acid, and 2-keto-4-(methylmercapto)-butyric acid has a greater heat stability with a residual activity of more than 50% after 90 minutes heating at 52° C. Here also there is observed an identical pattern of the desactivation kinetics for all tested substrates which permits the conclusion that these reactions are catalyzed by the same protein.

The molecular weight of the L-phenylalanine-dehydrogenase was ascertained by gel filtration on Sephacryl-S 300 superfine according to the procedure of Andrews (Meth. Biochemical Analysis, Volume 18, pages 1 to 53 (1970) and determined to 130,000±10.000 Dalton. As mobile phase there was employed 50 mM potassium phosphate buffer, pH 7.5, 100 mM sodium chloride. To stabilize the L-phenylalanine-dehydrogenase there was added to the mobile phase sufficient ammonium sulfate that there was present a 5% saturated solution. The reference proteins (catalase, bovine serum albumin, ovalbumin and chymotrypsinogen) were chromatographed under identical conditions. Under the conditions of the gel filtration there was observed a dissociation of the L-phenylalanine-dehydrogenase in subunits of 66,000±5,000 Dalton.

On the one hand the L-phenylalanine-dehydrogenase of the invention can be used in a manner known of itself to convert phenyl pyruvic acid, p-hydroxyphenyl pyruvic acid, indolyl pyruvic acid, or 2-keto-4-(methylmercapto)-butyric acid in the presence of ammonium ions and with NADH as coenzyme into the corresponding L-α-amino-carboxylic acids. On the other hand, the new enzyme can also be employed to determine enzymatically the concentration in aqueous solution of phenyl pyruvic acid or p-hydroxyphenyl pyruvic acid or of L-phenylalanine or L-tyrosine. The determination is very simple to carry out. The change of the adsorption of NADH at 340 nm is followed and then the concentration sought read off a corresponding standard curve.

BRIEF DESCRIPTION OF THE DRAWINGS

FIG. 1 is a graph summarizing data obtained in Example 2, and

FIG. 2 is a graph of the reaction rate as a function of pH.

The process can comprise, consist essentially of, or consist of the stated steps with the recited materials.

The invention is explained in more detail in the following examples. Unless otherwise indicated, all parts and percentages are by weight.

DETAILED DESCRIPTION

Example 1

Dehydrogenase Producers 14 samples of earth from various locations in the district Brunswick were made into a paste with sterile salt solution (0.9% NaCl). Aliquots of the aqueous supernatant were spread out on Petri dishes having solid culture medium and the Petri dishes incubated at 27° C. for 2 to 3 days. The culture medium was prepared as follows: 10 g L-phenylalanine, 4.8 g $K_2HPO_4.3H_2O$, 1.5 $KH_2PO_4$, 0.2 g $MgSO_4.7H_2O$, 2 mg $CaCl_2.2H_2O$, 0.4 mg $ZnSO_4.7H_2O$, 0.2 mg $FeCl_3.6H_2O$ and 20 g agar were dissolved to one liter with deionized water, the pH adjusted to 7.2 and the mixture sterilized. After cooling there was added 1 ml of sterile vitamin solution according to Schlegel and the culture medium poured into sterile Petri dishes. Organisms which showed good growth were purified via several dilution smears. Strains appearing uniform under the microscope were then grown in 100 ml of liquid medium in 500 ml Erlenmeyer flasks with two shikaues at 27° C. and the rotary shaking machine at 100 rpm. The liquid medium has the composition given above, but contains no agar. After 2 to 3 days the contents of the shaken flask were centrifuged and the sediment washed with 0.05M potassium phosphate buffer (pH 7.4). Resuspended cells were broken up with supersonics for 5 minutes. Insoluble cell components were separated off by centrifuging and the supernatant tested as an enzyme source.

57 strains were isolated from the 14 samples of earth which strains grew on L-phenylalanine as the sole carbon and nitrogen source. Of these one strain (Brevibacterium species DSM 2448) showed the desired enzyme activity. There was used a photometric test to detect the enzyme. As test additive there was used: 0.7M ammonium chloride/ammonium buffer (pH 8.5), 0.1 mM NADH, 10 mM phenyl pyruvate and limiting amount of enzyme (10 to 20 μg protein per test). The decrease of the adsorption of NADH at 340 nm was measured. A blank value was subtracted from the values obtained, which blank value would be obtained if the test were run without addition of phenyl pyruvate. The enzyme activity is stated in international units, whereby one unit signifies the decrease of 1μ mole NADH/min.

Brevibacterium species DSM 2448 grows in short gram positive rods, which with increasing age transfer into cocci form. The cells are immobile and do not form spores. Growth is carried out strictly aerobically. No acid is formed from glucose. Catalase and nitrate reduction are positive, splitting of urea positive, gelatin, casein and starch breakdown negative, $H_2S$-formation negative, growth at 41° C. negative. There were detected as all wall sugars arabinose mannose, and galactose.

Example 2

Production of the L-Phenylalanine-Dehydrogenase

Brevibacterium species DSM 2448 was grown in the following medium to produce the enzyme: glucose 5 grams, yeast extract 5 grams, malt extract 10 grams, L-phenylalanine 10 grams, $KH_2PO_4$ 3 grams The solid substrate was dissolved to one liter with deionized water, the pH of this solution was adjusted to 7.2 and it was sterilized for 15 minutes at 121° C. and 1 bar gauge pressure. Culturing was carried out in 500 ml Erlenmeyer flasks having two shikaues, filled with 100 ml of medium. Sterilized medium was inoculated by transferring a loop full of Brevibacterium species DSM 2448 from a slant agar tube. The medium was incubated at 27° C. for 20 to 23 hours on the rotary shaking machine having 120 rpm. The grown culture was centrifuged (15 minutes at 8000×gravity), the sediment suspended with 0.05M potassium phosphate buffer (pH 7.4). It was centrifuged again, the thus obtained washed sediment suspended in 0.05M potassium phosphate buffer (pH 7.4) so that per gram of wet cell mass there were used 4 ml of buffer. This suspension was subjected to ultrasonics on the ultrasonic apparatus (MSE, 150 Watt, MK 2) having 3 mm peaks with cooling in an ice bath 5×1 minute with pauses for cooling the suspension of at least 1 minute. After centrifugation (10 minutes at 12000×g), there was obtained a crude extract which customarily contains 1 to 2 mg of protein/ml and 3 to 6 units of L-phenylalanine-dehydrogenase/ml. It can be kept at −18° C., whereby after one month no loss of activity is detectible. In case it is desired, there can be removed lower molecular weight components from the crude extract by diafiltration or by gel chromatography over Sephadex G-25 column accordng to customary modes of operation.

The progress of the formation of enzyme during the growth was followed in the 1.5 liter fermenter (Biolafitte). The strain was grown in the production medium, for the inoculation there were used 30 ml of a 24 hour old seed culture.

Growth conditions: 30° C., aeration rate 60 l/h, turbine stirrer at 400 rpm.

In the samples there was measured;

(a) the optical density (turbidity) of the culture at 578 nm as a measure of the growth, (b) the L-phenylalanine content in the medium (after centrifuging off the cells) on the aminoacid analyzer (c) the centrifuged off cells were disintegrated and there was measured in the supernatant (crude extract) the activity of the PheDH (U/ml) as well as the protein content (mg/ml) and from this the specific enzyme activity (U/mg) and the volume activity of the pHeDH per 1 liter culture calculated.

The data are collected in FIG. 1.

The enzyme was formed in an early growth phase, the L-Phe-content in the medium drops with the appearance of the activity. A maximum activity is attained under these growth conditions after 30 to 35 hours, in the further course of time the enzyme content then drops to about 50% (65 hours).

Example 3

Production at the 70 Liter Scale 68 liters of product medium according to Example 2 were sterilized at 120° C. in a fermenter (100 liter volume, manufacturer Giovanola Freres SA Monthey) and after cooling inoculated with 2 liters of seed culture (grown 24 hours). The cultivation was carried out at 30° C. with an aeration rate of 1 vvm and with 200 rpm of the turbine stirrer. After 24 hours growth the cells were harvested by centrifugation. In all, there were obtained 5.9 kg of wet bacteria having a total enzyme content of 77,000 units. An aliquot of this cell mass was disintegrated according to Example 2 and the activity of the L-phenylalanine-dehydrogenase determined. The disintegrated sample showed a specific activity of 1.6 U/mg in the crude extract.

EXAMPLE 4

Induction of The L-Phenyalanine-Dehydrogenase

Brevibacterium species DSM 2448 was grown in a medium having 1% malt extract, 0.5% glucose, 2 μg thiamine/l, 0.3% $KH_2PO_4$ and different aminoacids, in each case 1%. Besides there was tested L-phenylalanine methyl ester (concentration in the medium 0.5%) as an inductor. The pH of the medium was 7.4 before beginning the cultivation. After 24 hours growth at 30° C. on the rotary shaking machine (120 rpm) the cells were centrifuged off, disintegrated with supersonics and the reductive amination of 5 α-ketocarboxylic acids tested for each extract in the optical test.

Additionally, there was followed the formation of L-tryptophane from indolyl pyruvate on the aminoacid analyzer. Indolyl pyruvate in the available quality (Sigma Company) shows too high an adsorption at 340 nm so that the optical test cannot be used.

The results are set forth in Table 1. Therein it is shown that in the Brevibacterium species DSM 2448 there are present two inducible aminoacid-dehydrogenases. The L-phenylalanine-dehydrogenase converts phenyl pyruvate, p-hydroxyphenyl pyruvate, indolyl pyruvate and 2-keto-4-(methylmercapto)-butyrate to the corresponding L-aminoacids phenylalanine, tyrosine, tryptophane, and methionine. This L-phenylaline dehydrogenase is induced by L-phenylalanine, D-phenylalanine, the racemate D,L-phenylalanine, L-phenylalanine methyl ester and L-histidine. It is remarkable that D-phenylalanine is a very good inductor. Furthermore it is remarkable that L-histidine acts as an inductor although the L-phenylalanine-dehydrogenase essentially does not utilize imidazolyl pyruvic acid as a substrate.

Example 5

20 ml of crude extract which is obtained by supersonic disintegration of 4 grams of Brevibacterium species DSM 2448 and subsequent centrifugation were treated with stirring with ammonium sulfate to give 40% of saturation and stirred for one hour at 4° C. Precipitated protein was centrifuged off at 15000×g (30 minutes). The supernatant (17.5 ml) was charged to a Sephacryl-S 300 column (2.5×85 cm) which was equilibrated with 40% saturated ammonium sulfate solution. By washing with 400 ml of 0.1M potassium phosphate buffer (pH 7.5) with 40% of saturation of ammonium sulfate, the main amount of protein was elated from this column. Under these conditions, the aminoacid-dehydrogenase remains bound on the Sephacryl column. If the ammonium sulfate concentration is lowered from 40% to 10% of saturation by establishing a gradient then the dehydrogenase is also eluted. This shows that first at about 32% of saturation with ammonium sulfate the L-leucine-dehydrogenase is eluted. Clearly separated thereto at about 26% of saturation with ammonium sulfate the L-phenylalanine-dehydrogenase is eluted. The eluate is collected in fraction of 3.6 ml. The L-phenylalanine-dehydrogenase containing fractions are combined and concentrated by ultrafiltration over a YM5-membrane. The purification is summarized in Table 2. The enzyme can be stably stored for a long time at 4° C. in the presence of 20% ammonium sulfate.

TABLE 2

| Purification Step | Volume ml | Protein mg | Total Activity U | Specific Activity U/mg | Yield % | Enrichment factor |
|---|---|---|---|---|---|---|
| Crude Extract | 20 | 130 | 85 | 0,65 | | |
| Supernatant 40% Ammonium sulfate saturation | 16,5 | 101 | 81 | 0,80 | 95 | 1,2 |
| Peak II | 108 | 1,62 | 55 | 34 | 65 | 52 |

TABLE 2-continued

| Purification Step | Volume ml | Protein mg | Total Activity U | Specific Activity U/mg | Yield % | Enrichment factor |
|---|---|---|---|---|---|---|
| Sephacryl-Column | | | | | | |

Example 6

Purification of the L-Phenylalanine-Dehydrogenase

Alternatively to Example 5 Brevibacterium species DSM 2448 can be disintegrated on an industrial scale in a glass bead mill. As an example 270 grams of cells were disintegrated in a Dyno-Mill Type KDL and the cell fragments separated off with the help of an aqueous 2-phase system (according to German Pat. No. 2,639,129). The system used has the composition 20% w/w cells, 18% w/w polyethylene glycol 1540 and 7% w/w potassium phosphate, pH 8.0. The L-phenylalanine-dehydrogenase can be extracted completely into the polyethylene glycol rich upper phase (1073 ml).

The enzyme containing upper phase was diluted with 50 mM of potassium phosphate buffer (pH 7.5) which was 30% saturated with ammonium sulfate and diafiltered using an Amicon Hollow fiber modul (H1P50), whereby foreign protein and polyethylene glycol 1540 were removed. The diafiltrate (250 ml) was charged to a Sepharose 4B-column (5×20 cm) which was equilibrated with 50 mM of potassium phosphate buffer (pH 7.5) which was 40% saturated with ammonium sulfate. The main amount of protein was eluted from this column by washing with this buffer (1 liter), while under these conditions the L-phenylalanine-dehydrogenase remains on the column. The enzyme was eluted by establishing a gradient corresponding to Example 5 and subsequently concentrated. The purification according to this method is summarized in Table 3.

4.0 mM of L-phenylalanine and 3 mM NAD+ in a 0.1M glycine/NaCl buffer at different pH values. There were established several pH values in the range 6.0 to 10.5 by addition of hydrochloric acid or aqueous sodium hydroxide to the glycine/NaCl buffer before mixing together the test mixture.

The results are likewise summarized in FIG. 2. The reverse reaction increased up to pH 10.5.

Example 8

Dependency of the Reaction Rate On the Substrate Concentrations

The relationship of the speed of reaction of the reductive amination of phenyl pyruvate to L-phenylalanine for the substrate NADH was investigated in the following test mixture:

0.7M ammonium chloride/ammonium buffer (pH 8.5), 10 mM phenyl pyruvate, limiting amounts of enzyme (crude extract according to Example 2, 20 μg protein per test). The NADH concentration in the test mixture was varied in the range of 0.025 to 0.35 mM.

It was shown that the optimum speed of reaction was attained at 0.3 mM. The $K_m$ value for NADH amounts to 0.064 mM.

The dependency of the speed of reaction of the reductive amination of phenyl pyruvate to L-phenylalanine on the ammonium ion concentration was investigated in the following test mixture:

10 mM phenyl pyruvate, 0.2 mM NADH, limiting amounts of enzyme (crude extract according to Exam-

TABLE 3

| Purification Step | Volume ml | Protein mg | Total Activity U | Specific Activity U/mg | Yield % | Enrichment factor |
|---|---|---|---|---|---|---|
| Crude extract | 650 | 7735 | 6292 | 0,81 | 100 | 1 |
| Top-Phase I | 1073 | 5258 | 6373 | 1,21 | 101 | 1,5 |
| Diafiltration | 250 | 3226 | 3632 | 1,13 | 58 | 1,4 |
| Sepharose 4 B | 210 | 206 | 2680 | 13,0 | 43 | 16,0 |

Example 7

Dependency of the Reaction rate on pH

The speed of reaction of the reductive amination of phenyl pyruvate to L-phenylalanine in the presence of L-phenylalanine-dehydrogenase was investigated in relation to the pH of the reaction solution. The test mixture had the following composition:

0.1 mM NADH, 10 mM phenyl pyruvate and limiting amounts of enzyme (crude extract according to Example 2, 20 μg protein per test) in a 0.7M ammonium chloride solution at different pH values. The pH values chosen between 6.75 and 9.0 were established by addition of ammonia or hydrochloric acid before mixing together the test mixture.

In FIG. 2 there is plotted the speed of reaction as a function of the pH. The optimum pH is at 8.5.

The speed of reaction of the oxidative desamination of L-phenylalanine, catalyzed by the L-phenylalanine-dehydrogenase was likewise investigated in relation to the pH value. The test mixture had the following composition:

ple 2, 20 μg protein per test). There was employed an ammonium chloride buffer whose pH was regulated to pH 8.5 with ammonia. The ammonium chloride molarity in the test varied in the range from 0.095 to 0.7M.

It was shown that the speed of reaction increases until at least 0.5M ammonium chloride. 0.7M ammonium chloride does not act inhibitory and therefore was regarded as optimum for the test of enzyme.

The reductive amination of various α-ketocarboxylic acids was investigated in relation to the ketoacid concentration. For this purpose there was used the following test mixtures:

0.7M ammonium chloride/ammonium buffer (pH 8.5), 0.2 mM NADH, limiting amounts of enzyme (1 μg purified protein according to Example 5). The ketoacid concentration was varied in each case within the range of 0.01 to 30 mM.

The initial speed of reaction (adsorption 340 nm/minute) was evaluated according to Michaelis-Menten. The found $K_m$ and $V_{max}$ values are collected in Table 4. Because of the disturbance of the optical test in the case of the substrate indolyl pyruvate, in the reductive amination of indolyl pyruvate to L-tryptophane the amount of L-tryptophane formed was determined as a function of the time on the aminoacid analyzer (Biotronik BC 6000, equipped with an Integrator Biotronik, System 1, in a 1-column program, as standard solution there was used an aminoacid-standard IV of the Pierce company).

TABLE 4

$K_m$-and $V_{max}$-Value With Purified PheDH
(0.055 mg Protein/ml)

| Substrate | $K_m$ [mM] | $V_{max}$ [U/ml] |
|---|---|---|
| Phenylpyruvate | 0.11 | 1.82 |
| p-Hydroxyphenylpyruvate | 0.24 | 1.75 |
| 2-Keto-4-(methylmercapto)-butyrate | 3.0 | 1.08 |
| Indolylpyruvate | 8.0 | 0.44 |

The dependency of the speed of reaction of the oxidative desamination of L-phenylalanine on the NAD+ concentration was investigated in the following test mixture:

0.1M glycine-NaCl/NaOH buffer (pH 10.7) 4 mM L-phenylalanine, limiting amounts of enzyme (20 µg protein purified according to Example 6).

The NAD+ concentration was varied in the range of 0.1 to 5.0 mM. It was shown that the optimum conversion was reached at a concentration of 3 mM.

The dependency of the speed of reaction of the oxidation desamination on the L-phenylalanine concentration was investigated in the following test mixture:

0.1M glycine-NaCl/NaOH buffer (pH 10.7) 3 mM NAD+, limiting amounts of enzyme (20 µg protein purified according to Example 6). The phenylalanine concentration was varied in the range of 0.3 to 15 mM.

The NADH formed in the reaction was measured at 340 nm. The initial speed of reaction was evaluated according to Michaelis-Menten. The $K_m$ value for phenylalanine amounts to 0.8 mM, the maximum speed of reaction is 1.02 U/mg.

Example 9

Production of L-phenylalanine, L-Tyrosine, L-Tryptophan, and L-Methionine by Reductive Amination of the Analogous α-Ketocarboxylic Acids In order to regenerate the NADH consumed in the reductive amination there was added to the reaction mixture an excess of ammonium formate and the enzyme formate-dehydrogenase (E.C. 1.2.1.2) which in the oxidation of formate to $CO_2$ reduces the cosubstrate NAD+ to NADH.

The reductive amination of a series of α-ketocarboxylic acids was tested under comparable conditions. The test mixture contained thereby uniformly 400 mM of ammonium formate (pH 8.5), 0.3 mM NADH, 0.6 U/ml formate-dehydrogenase (prepared according to Kroner et al (1982), J. Chem. Tech. Biotechnol, Volume 32, pages 130 to 137), 0.5 U/ml L-phenylalanine-dehydrogenase, 25 mM α-ketocarboxylic acid. The total volume was 3 ml. The incubation was carried out with stirring at 27° C. The product formation in each case was followed on the aminoacid analyzer. The results are set forth in Table 5. Phenyl pyruvate, p-hydroxyphenyl pyruvate, indolyl pyruvate and 2-keto-4-(methylmercapto)-butyrate were converted well. In contrast imidazolyl pyruvate was practically not utilized as a substrate.

TABLE 5

| | | Product Formation after | | | |
|---|---|---|---|---|---|
| | | 2 hours | | 6 hours | |
| Substrate | Product | mM | % | mM | % |
| Phenyl pyruvic acid | L-Phenylalanine | 12,5 | (50) | 16,6 | (66) |
| p-Hydroxyphenyl pyruvic acid | L-Tyrosine | 10,2 | (41) | 14,8 | (59) |
| Indolyl pyruvic acid | L-Tryptophan | 6,2 | (25) | 12,0 | (48) |
| Imidazolyl pyruvic acid | L-Histidine | 0,2 | (1) | 0,5 | (2) |
| 2-Keto-4-(methylmercapto)-butyric acid | L-Methionine | 12,8 | (51) | 15,6 | (62) |

Example 10

Continuous Production of L-Phenylalanine

It is possible to continuously synthesize phenalyalanine from phenyl pyruvate in an enzyme membrane reactor using molecular weight enlarged NADH bound to polyethylene glycoe (PEG). The PEG-NADH was produced according to German Pat. No. 2,841,414. The modified coenzyme and the enzyme formate-dehydrogenase employed and L-phenylalanine-dehydrogenase were retained in the reactor by an ultrafiltration membrane YM5 (product of the Amicon Company, Witten) while the lower molecular weight components of the reaction solution, unreacted substrate and the L-phenylalanine formed were continuously removed from the reactor. The reactor volume was held constant while phenyl pyruvate and ammonium formate were metered in from a reservoir to the same extent that the ultrafiltrate left the reactor. The reactor volume was 10 ml, the concentration of PEG-NADH 0.3 mM. There were injected into the reactor 20 units of formate-dehydrogenase and 20 units of L-phenylalanine-dehydrogenase. The substrate solution contained 400 mM of ammonium formate at pH 8.3 and 20 mM phenyl pyruvate (sodium salt).

The reaction solution was continuously circulated over the membrane at 30 ml/hour with a peristaltic pump. There were obtained about 4 ml of ultrafiltrate per hour. This corresponds to a residence time of 2.5 hours. With this research construction there can be put through in the course of 110 hours 9.8 mmoles (1.83 grams) of sodium phenyl pyruvate. The ultrafiltrate was collected in fractions and the content of L-phenylalanine determined on the aminoacid analyzer. Over a time span of 110 hours on the average 70% of the phenyl pyruvate was converted to L-phenylalanine, in the combined ultrafiltrates there were measured 6.9 mmoles (1.14 grams) of L-phenylalanine. The reaction product obtained in this example is relatively simple to purify, since the solution is contaminated only with unconverted phenyl pyruvate and ammonium formate. The ultrafiltrate (450 ml, 1.14 grams of L-phenylalanine) was lyophilized, taken up with 50 ml of 0.5M formic acid and an aliquot of 12.5 ml charged to an ion exchange column (Biorad AG 50 W X 8, 200 to 400 mesh H+ form 1×10 cm). The column was washed with 100 ml of 0.5 m formic acid. under these conditions phenyl pyruvate was not bound. By a color reaction with iron-(III)-chloride solution (7.5% pH 2.5, measuring the adsorption at 436 nm) it could be shown that phenyl pyruvate was removed after the passing of 20 to 25 ml of wash solution. L-phenylalanine was eluted from the ion exchanger with a 5% pyridine solution. Under these circumstances ammonium ions remain bound on the ion exchanger so that the L-phenylalanine detection in the eluate is possible with ninhydrin. The exchanger was regenerated by treatment with 4N hydrochloric acid and was employed again after washing with deionized water. The phenylalanine containing eluates were combined and concentrated to dryness on the rotary evaporator. For complete removal of the pyridine, the concentrate was taken up several times with water. In this manner there was isolated 1.12 grams of L-phenylalanine, which was employed for further analytical determinations.

Aminoacid Analysis: The aminoacid analyzer showed that the product from Example 10 contained no aminoacids other than the L-phenylalanine.

Optical Rotation: There was employed a Perkin-Elmer Polarimeter Type 241 for the measurements. The measurements were carried out at 436 nm, pH 2.1 and 30° C. A standard curve with L-phenylalanine shows a linear relationship of rotary value and cncentration between 5 and 100 mM. The rotary value of the sample synthesized in Example 10 was −0.371° in a 71 mM solution (concentration determination via the aminoacid analyzer). A comparison with the standard curve shows that optically pure L-phenylalanine was obtained.

Test on D-Aminoacid By Means of D-Aminoacid Oxidase (D-AOD): D-AOD isolated from pigs (product Boehringer Mannheim GmbH) is specific for D-aminoacids. The hydrogen peroxide formed in the oxidation of the D-aminoacids with D-AOD is converted with the help of the enzyme peroxidase to a leuco dyestuff. There was plotted a calibration curve with D-phenylalanine which in the range from 0.01 to 0.35 mM shows a linear relationship between the difference of the adsorption values at 436 nm and the concentration of D-phenylalanine. The limit of detection is at 0.005 mM. The sample employed (55 mM of L-phenylalanine according to Example 10 was inactive in this test. Impurities in the L-phenylalanine by the D-enantiomer therefore must be below 0.01%.

The entire disclosure of German priority application No. P 3307095.4 is hereby incorporated by reference.

What is claimed is:

1. L-phenylalanine-dehydrogenase having the following properties:
    (a) it catalyzes the reductive amination of phenyl pyruvic acid to L-phenylalanine in the presence of ammonium ions and with NADH (nicotinamide-adenine-dinucleotide) as coenzyme.,
    (b) it catalyzes the reductive amination of α-ketocarboxylic acids to the corresponding α-aminocarboxylic acids, including p-hydroxyphenyl pyruvic acid to L-tyrosine, indolyl pyruvic acid to L-tryptophane and 2-keto-4-(methylmercapto)-butyric acid to L-methionine, in the presence of ammonium ions and with NADH as coenzyme,
    (c) it catalyzes the oxidative desamination of L-phenylalanine, 1-tyrosine, L-tryptophane and L-methionine with NAD+ as coenzyme,
    (d) it has an optimum pH region for the reductive amination of 8.5±1, and
    (e) it has an optimum pH region for the oxidative desamination of 10±1.

2. L-phenylalanine-dehydrogenase according to claim 1 produced microbiologically.

3. L-phenylalanine-dehydrogenase according to claim 2 produced by growing Brevibacterium species DSM 2448 on an appropriate medium.

4. A process for obtaining the L-phenylalanine-dehydrogenase enzyme of claim 1 comprising aerobically cultivating Brevibacterium species DSM 2448 in an aqueous culture containing a source of carbon and nitrogen, thiamine, mineral salts and an inductor at a pH between 6.5 and 7.5 and at a temperature of 25° to 32° C., separating off the cell mass and recovering the enzyme from the isolated cells.

5. A process according to claim 4 wherein there is employed as the inductor L-phenylalanine, D-phenylalanine, D,L-phenylalanine, a D,L-phenylalanine ester or L-histidine.

6. A process according to claim 5 wherein the cells are mechanically disintegrated, the insoluble cell debris separated off and the enzyme concentration is enriched.

7. A process according to claim 4 wherein the cells are mechanically disintegrated, the insoluble cell debris separated off and the enzyme concentration is enriched.

8. A process according to claim 7 wherein the enrichment is carried out by fractional salt precipitation.

9. A process according to claim 6 wherein the enrichment is carried out by fractional salt precipitation.

10. A process according to claim 6 wherein the enrichment is carried out by chromatographic separation.

11. A process according to claim 7 wherein the enrichment is carried out by chromatographic separation.

12. A process of converting a compound which is phenyl pyruvic acid, p-hydroxyphenyl pyruvic acid, indolyl pyruvic acid or 2-keto-4-(methylmercapto)-butyric acid into the corresponding L-α-aminocarboxylic acid comprising reductively aminating the compound in the presence of the L-phenylalanine-dehydrogenase of claim 1.

13. A process according to claim 12 wherein the reductive amination is carried out in the presence of ammonium ions and NADH as a coenzyme.

14. A process according to claim 13 wherein the reductive amination is carried out at a pH of 7.5 to 9.5.

15. A process according to claim 12 wherein the compound is phenyl pyruvic acid.

16. A process according to claim 12 wherein the compound is p-hydroxyphenyl pyruvic acid.

17. A process according to claim 12 wherein the compound is indolyl pyruvic acid.

18. A process according to claim 12 wherein the compound is 2-keto-4-(methylmercapto)-butyric acid.

19. L-phenylalanine dehydrogenase according to claim 1 having the property of being able to be produced by growing Brevibacterium species DSM 2448 on an appropriate medium.

* * * * *